US007135278B1

(12) United States Patent
Zauderer

(10) Patent No.: US 7,135,278 B1
(45) Date of Patent: Nov. 14, 2006

(54) METHOD OF SCREENING FOR THERAPEUTICS FOR INFECTIOUS DISEASES

(75) Inventor: Maurice Zauderer, Pittsford, NY (US)

(73) Assignee: University of Rochester, Rochester, NY (US)

(*) Notice: Subject to any disclaimer, the term of this patent is extended or adjusted under 35 U.S.C. 154(b) by 0 days.

(21) Appl. No.: 09/966,746

(22) Filed: Oct. 1, 2001

Related U.S. Application Data

(60) Provisional application No. 60/236,381, filed on Sep. 29, 2000.

(51) Int. Cl.
| | |
|---|---|
| *C12Q 1/00* | (2006.01) |
| *G01N 33/00* | (2006.01) |
| *G01N 33/50* | (2006.01) |
| *A61K 39/00* | (2006.01) |
| *A61K 39/04* | (2006.01) |
| *A61K 39/12* | (2006.01) |

(52) U.S. Cl. ................. 435/4; 435/5; 435/6; 424/184.1
(58) Field of Classification Search ............ 424/184.1, 424/186.1, 188.1, 450, 277.1, 9.1, 9.2; 435/4, 435/5, 6, 7.1, 7.2, 8, 320.1, 325; 514/44, 514/2; 530/350, 351, 387.1, 387.9, 388.1, 530/389.1; 536/22.1, 23.1, 23.4, 23.5, 23.51, 536/23.53, 23.72, 23.74, 24.3, 24.31, 24.32, 536/26.6
See application file for complete search history.

(56) References Cited

U.S. PATENT DOCUMENTS

| | | | |
|---|---|---|---|
| 5,500,362 A | 3/1996 | Robinson et al. | |
| 5,525,471 A | 6/1996 | Zeng | |
| 5,700,644 A | 12/1997 | Gould et al. | |
| 5,721,351 A * | 2/1998 | Levinson ....................... | 435/8 |
| 5,827,658 A | 10/1998 | Liang | |
| 5,879,892 A * | 3/1999 | Van Baren et al. ............. | 435/6 |
| 6,004,755 A * | 12/1999 | Wang ............................ | 435/6 |
| 6,033,860 A | 3/2000 | Lockhart et al. | |
| 6,045,996 A | 4/2000 | Cronin et al. | |
| 6,060,240 A | 5/2000 | Kamb et al. | |
| 6,060,288 A | 5/2000 | Adams et al. | |
| 6,312,909 B1 * | 11/2001 | Shyjan ..................... | 435/252.3 |
| 6,399,328 B1 * | 6/2002 | Vournakis et al. ........ | 435/320.1 |
| 6,706,477 B1 | 3/2004 | Zauderer | |
| 6,800,442 B1 | 10/2004 | Zauderer | |
| 6,872,518 B1 | 3/2005 | Zauderer | |
| 2002/0155447 A1 | 10/2002 | Zauderer et al. | |
| 2003/0022157 A1 | 1/2003 | Zauderer et al. | |
| 2003/0194696 A1 | 10/2003 | Zauderer et al. | |
| 2004/0063907 A1 | 4/2004 | Zauderer et al. | |

FOREIGN PATENT DOCUMENTS

| | | |
|---|---|---|
| WO | WO 98/46638 | 10/1998 |
| WO | WO 02/27027 A2 | 4/2002 |
| WO | WO 02/31117 A2 | 4/2002 |

OTHER PUBLICATIONS

Tanaka et al., "Genome-wide Expression Profiling of Mid-gestation Placenta and Embryo using a 15,000 Mouse Developmental cDNA Library," Proceedings of the National Academy of Sciences, vol. 97, pp. 9127-9132.*
Hernández et al., Proceedings of the National Academy of Sciences USA, vol. 99 No. 19, pp. 12275-12280 ( Sep. 2002).*
Herberts et al., Human Immunology, 64: 44-55 (2003- submitted by Applicant in the Response of Oct. 2003).*
Hickman et al., Journal of Immunology, 171: 22-26 (2003- submitted by Applicant in the Response of Oct. 2003).*
An, D.S., et al., "High-Efficiency Transduction of Human Lymphoid Progenitor Cells and Expression in Differentiated T Cells," *J. Virol.* 71:1397-1404, American Society for Microbiology (1997).
Bennink, J.R., and Yewdell, J.W., "Recombinant Vaccinia Viruses as Vectors for Studying T Lymphocyte Specificity and Function," *Curr. Top. Microbiol. Immunol.* 163:153-184, Springer-Verlag (1990).
Bloom, M.B., et al., "Identification of Tyrosinase-related Protein 2 as a Tumor Rejection Antigen for the B16 Melanoma," *J. Exp. Med.* 185:453-459, Rockefeller University Press (1997).
Blum-Tirouvanziam, U., et al., "Localization of HLA-A2.1-Restricted T Cell Epitopes in the Circumsporozoite Protein of *Plasmodium falciparum,*" *J. Immunol.* 154:3922-3931, The American Association of Immunologists (1995).
Boël, P., et al., "BAGE: a New Gene Encoding an Antigen Recognized on Human Melanomas by Cytolytic T Lymphocytes," *Immunity* 2:167-175, Cell Press (1995).
Bowtell, D.D.L., "Options available—from start to finish—for obtaining expression data by microarray," *Nat. Genet.* (*Supplement*) 21:25-32, Nature Publishing Co. (Jan. 1999).
Brichard, V., et al., "The Tyrosinase Gene Codes for an Antigen Recognized by Autologous Cytolytic T Lymphocytes on HLA-A2 Melanomas," *J. Exp. Med.* 178:489-495, Rockefeller University Press (1993).
Butera, S.T., et al., "Human Immunodeficiency Virus Type 1 RNA Expression by Four Chronically Infected Cell Lines Indicates Multiple Mechanisms of Latency," *J. Virol.* 68:2726-2730, American Society for Microbiology (1994).
Cannon, P., et al., "Analysis of Tat Function in Human Immunodeficiency Virus Type 1-Infected Low-Level-Expression Cell Lines U1 and ACH-2," *J. Virol.* 68:1993-1997, American Society for Microbiology (1994).
Chaux, P., et al., "Identification of Five MAGE-A1 Epitopes Recognized by Cytolytic T Lymphocytes Obtained by In Vitro Stimulation with Dendritic Cells Transduced with *MAGE-A1,*" *J. Immunol.* 163:2928-2936, The American Association of Immunologists (Sep. 1999).

(Continued)

Primary Examiner—Bruce R. Campell
Assistant Examiner—Zachariah Lucas
(74) Attorney, Agent, or Firm—Sterne, Kessler, Goldstein & Fox P.L.L.C.

(57) ABSTRACT

The present invention relates to a method of screening for a host cell gene products which are useful as therapeutics for an infective disease. This method comprises identifying genes which are differentially expressed in infected cells, and screening the differentially expressed gene products for immunogenicity.

13 Claims, 1 Drawing Sheet

OTHER PUBLICATIONS

Cheung, V.G., et al., "Making and reading microarrays," *Nat. Genet. 21 (Supplement)*:15-19, Nature Publishing Co. (Jan. 1999).

DeRisi, J., et al., "Use of a cDNA microarray to analyse gene expression patterns in human cancer," *Nat. Genet. 14*:457-460, Nature Publishing Co. (1996).

Duggan, D.J., et al., "Expression profiling using cDNA microarrays," *Nat. Genet. 21 (Supplement)*:10-14, Nature Publishing Co. (Jan. 1999).

Eisen, M.B., and Brown, P.O., "DNA Arrays for Analysis of Gene Expression," *Methods Enzymol. 303*:179-205, Academic Press (Jun. 1999).

Gaugler, B., et al., "Human Gene MAGE-3 Codes for an Antigen Recognized on a Melanoma by Autologous Cytolytic T Lymphocytes," *J. Exp. Med. 179*:921-930, The Rockefeller University Press (1994).

Geiss, G.K., et al., "Large-Scale Monitoring of Host Cell Gene Expression during HIV-1 Infection Using cDNA Microarrays," *Virology 266*:8-16, Academic Press (Jan. 2000).

Kawakami, Y., et al., "Cloning of the gene coding for a shared human melanoma antigen recognized by autologous T cells infiltrating into tumor," *Proc. Natl. Acad. Sci. USA 91*:3515-3519, National Academy of Sciences (1994).

Kawakami, Y., et al., "Identification of a human melanoma antigen recognized by tumor-infiltrating lymphocytes associated with *in vivo* tumor rejection," *Proc. Natl. Acad. Sci. USA 91*:6458-6462, National Academy of Sciences (1994).

Liang, P., and Pardee, A.B., "Differential Display of Eukaryotic Messenger RNA by Means of the Polymerase Chain Reaction," *Science 257*:967-971, American Association for the Advancement of Science (1992).

Linsley, P.S., "Immunosuppression in Vivo by a Soluble Form of the CTLA-4 T Cell Activation Molecule," *Science 257*:792-795, American Association for the Advancement of Science (1992).

Lipshutz, R.J., et al., "High density synthetic oligonucleotide arrays," *Nat. Genet. 21 (Supplement)*:20-24, Nature Publishing Co. (Jan. 1999).

Lisitsyn, N., et al., "Cloning the Differences Between Two Complex Genomes," *Science 259*:946-951, American Association for the Advancement of Science (1993).

Merchlinsky, M., and Moss, B., "Introduction of Foreign DNA into the Vaccinia Virus Genome by *in Vitro* Ligation: Recombination-Independent Selectable Cloning Vectors," *Virology 190*:522-526, Academic Press (1992).

Merchlinsky, M., et al., "Construction and Characterization of Vaccinia Direct Ligation Vectors," *Virology 238*:444-451, Academic Press (1997).

Parker, K.C., et al., "Scheme for Ranking Potential HLA-A2 Binding Peptides Based on Independent Binding of Individual Peptide Side-Chains," *J. Immunol. 152*:163-175, The American Association of Immunologists (1994).

Planelles, V., et al., "Fate of the Human Immunodeficiency Virus Type 1 Provirus in Infected Cells: a role for *vpr*," *J. Virol. 69*:5883-5889, American Society for Microbiology (1995).

Reddy, A., et al., "A Monocyte Conditioned Medium Is More Effective Than Defined Cytokines in Mediating the Terminal Maturation of Human Dendritic Cells," *Blood 90*:3640-3646, The American Society of Hematology (1997).

Ressing, M.E., et al., "Human CTL Epitopes Encoded by Human Papillomavirus Type 16 E6 and E7 Identified Through In Vivo and In Vitro Immunogenicity Studies of HLA-A*0201-Binding Peptides," *J. Immunol. 154*:5934-5943, The American Association of Immunologists (1995).

Rosenblatt, J.D., et al., "Transactivation of Cellular Genes by Human Retroviruses," *Curr. Top. Microbiol. Immunol. 193*:25-49, Springer-Verlag (1995).

Scheiflinger, F., et al., "Construction of chimeric vaccinia viruses by molecular cloning and packaging," *Proc. Natl. Acad. Sci. USA 89*:9977-9981, National Academy of Sciences (1992).

Schena, M., et al., "Quantitative Monitoring of Gene Expression Patterns with a Complementary DNA Microarray," *Science 270*:467-470, American Association for the Advancement of Science (1995).

Schena, M., et al., "Parallel human genome analysis: Microarray-based expression monitoring of 1000 genes," *Proc. Natl. Acad. Sci. USA 93*:10614-10619, National Academy of Sciences (1996).

Scheuring, U.J., et al., "Early modifications of host cell gene expression induced by HIV-1," *AIDS 12*:563-570, Lippincott-Raven Publishers (1998).

Schönbach, C., et al., "Identification of HTLV-1-Specific CTL Directed against Synthetic and Naturally Processed Peptides in HLA-B*3501 Transgenic Mice," *Virology 226*:102-112, Academic Press (1996).

Shattock, R.J., et al., "Release of Human Immunodeficiency Virus by THP-1 Cells and Human Macrophages Is Regulated by Cellular Adherence and Activation," *J. Virol. 67*:3569-3575, American Society for Microbiology (1993).

Shimonkevitz, R., et al., "Antigen Recognition by H-2-Restricted T Cells: I. Cell-free antigen processing," *J. Exp. Med. 158*:303-316, The Rockefeller University Press (1983).

Shirai, M., et al., "CTL Responses of HLA-A2.1-Transgenic Mice Specific for Hepatitis C Viral Peptides Predict Epitopes for CTL of Humans Carrying HLA-A2.1," *J. Immunol. 154*:2733-2742, The American Association of Immunologists (1995).

Van den Eynde, B., et al., "The Gene Coding for a Major Tumor Rejection Antigen of Tumor P815 Is Identical to the Normal Gene of Syngeneic DBA/2 Mice," *J. Exp. Med. 173*:1373-1384, The Rockefeller University Press (1991).

Van den Eynde, B., et al., "A New Family of Genes Coding for an Antigen Recognized by Autologous Cytolytic T Lymphocytes on a Human Melanoma," *J. Exp. Med. 182*:689-698, The Rockefeller University Press (1995).

Van der Bruggen, P., et al., "A Gene Encoding an Antigen Recognized by Cytolytic T Lymphocytes on a Human Melanoma," *Science 254*:1643-1647, American Association for the Advancement of Science (1991).

Wentworth, P.A., et al., "Differences and similarities in the A2.1-restricted cytotoxic T cell repertoire in humans and human leukocyte antigen-transgenic mice," *Eur. J. Immunol. 26*:97-101, VCH Verlagsgesellschaft mbH (1996).

Könen-Waisman, S., et al., "Self Heat-Shock Protein (hsp60) Peptide Serves in a Conjugate Vaccine against a Lethal Pneumococcal Infection," *J. Infect. Dis. 179*:403-413, University of Chicago Press (Feb. 1999).

di Marzo Veronese, F., et al., "Autoreactive Cytotoxic T Lymphocytes in Human Immunodeficiency Virus Type 1-Infected Subjects," *J. Exp. Med. 183*:2509-2516, Rockefeller University Press (1996).

Overwijk, W.W., et al., "Vaccination with a recombinant vaccinia virus encoding a "self" antigen induces autoimmune vitiligo and tumor cell destruction in mice: Requirement for CD4$^+$ T lymphocytes," *Proc. Natl. Acad. Sci. USA 96*:2982-2987, National Academy of Sciences (Mar. 1999).

\* cited by examiner

Figure 1. Screening for differential gene expression in HIV infected cells
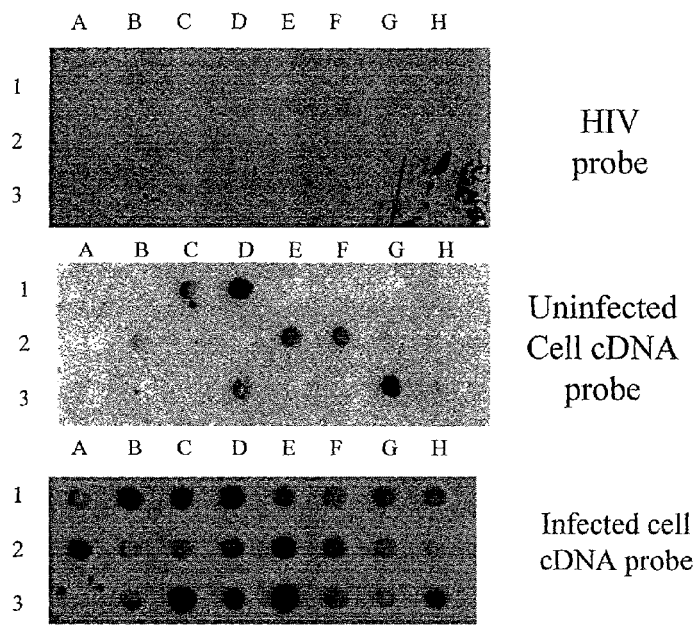
Figure 2. Differential gene expression in HIV infected cells
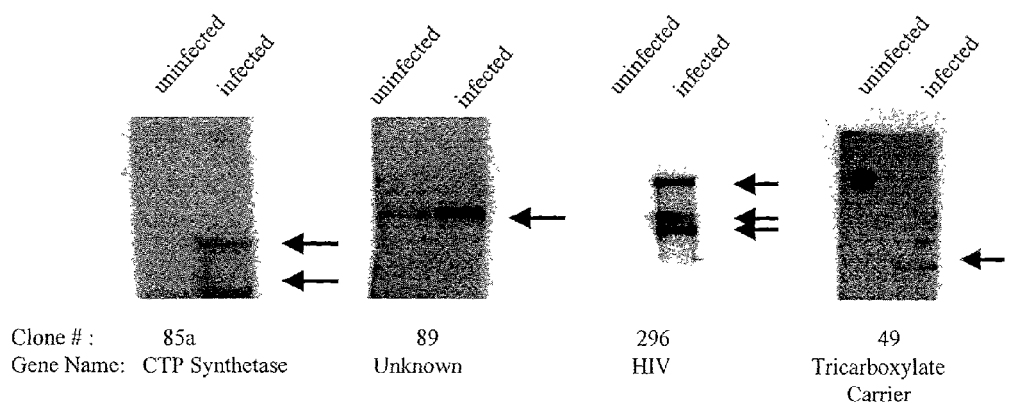

SEQUENCE LISTING

```
<160> NUMBER OF SEQ ID NOS: 12

<210> SEQ ID NO 1
<211> LENGTH: 10
<212> TYPE: DNA
<213> ORGANISM: Artificial Sequence
<220> FEATURE:
<223> OTHER INFORMATION: Oligonucleotide primer

<400> SEQUENCE: 1
tacaacgagg                                                          10

<210> SEQ ID NO 2
<211> LENGTH: 10
<212> TYPE: DNA
<213> ORGANISM: Artificial Sequence
<220> FEATURE:
<223> OTHER INFORMATION: Oligonucleotide primer

<400> SEQUENCE: 2
gtcagagcat                                                          10

<210> SEQ ID NO 3
<211> LENGTH: 10
<212> TYPE: DNA
<213> ORGANISM: Artificial Sequence
<220> FEATURE:
<223> OTHER INFORMATION: Oligonucleotide primer

<400> SEQUENCE: 3
ggaccaagtc                                                          10

<210> SEQ ID NO 4
<211> LENGTH: 10
<212> TYPE: DNA
<213> ORGANISM: Artificial Sequence
<220> FEATURE:
<223> OTHER INFORMATION: Oligonucleotide primer
```

```
<400> SEQUENCE: 4
tcagacttca                                                              10

<210> SEQ ID NO 5
<211> LENGTH: 10
<212> TYPE: DNA
<213> ORGANISM: Artificial Sequence
<220> FEATURE:
<223> OTHER INFORMATION: Oligonucleotide primer

<400> SEQUENCE: 5
tacctatggc                                                              10

<210> SEQ ID NO 6
<211> LENGTH: 10
<212> TYPE: DNA
<213> ORGANISM: Artificial Sequence
<220> FEATURE:
<223> OTHER INFORMATION: Oligonucleotide primer

<400> SEQUENCE: 6
tcggtcacag                                                              10

<210> SEQ ID NO 7
<211> LENGTH: 10
<212> TYPE: DNA
<213> ORGANISM: Artificial Sequence
<220> FEATURE:
<223> OTHER INFORMATION: Oligonucleotide primer

<400> SEQUENCE: 7
atctggtaga                                                              10

<210> SEQ ID NO 8
<211> LENGTH: 10
<212> TYPE: DNA
<213> ORGANISM: Artificial Sequence
<220> FEATURE:
<223> OTHER INFORMATION: Oligonucleotide primer

<400> SEQUENCE: 8
cttatccacg                                                              10

<210> SEQ ID NO 9
<211> LENGTH: 10
<212> TYPE: DNA
<213> ORGANISM: Artificial Sequence
<220> FEATURE:
<223> OTHER INFORMATION: Oligonucleotide primer

<400> SEQUENCE: 9
catgtctcaa                                                              10

<210> SEQ ID NO 10
<211> LENGTH: 10
<212> TYPE: DNA
<213> ORGANISM: Artificial Sequence
<220> FEATURE:
<223> OTHER INFORMATION: Oligonucleotide primer

<400> SEQUENCE: 10
gatcaagtct                                                              10

<210> SEQ ID NO 11
```

-continued

```
<211> LENGTH: 10
<212> TYPE: DNA
<213> ORGANISM: Artificial Sequence
<220> FEATURE:
<223> OTHER INFORMATION: Oligonucleotide primer

<400> SEQUENCE: 11
tgtcacatac                                                              10

<210> SEQ ID NO 12
<211> LENGTH: 10
<212> TYPE: DNA
<213> ORGANISM: Artificial Sequence
<220> FEATURE:
<223> OTHER INFORMATION: Oligonucleotide primer

<400> SEQUENCE: 12
ctgatccatg                                                              10
```

METHOD OF SCREENING FOR THERAPEUTICS FOR INFECTIOUS DISEASES

CROSS-REFERENCE TO RELATED APPLICATIONS

This application claims priority benefit of U.S. Provisional Appl. No. 60/236,381, filed Sep. 29, 2000, the entire disclosure of which is incorporated by reference herein.

BACKGROUND OF THE INVENTION

1. Field of the Invention

The present invention relates to methods of identifying therapeutics useful for infectious diseases. More specifically, the present invention relates to methods of identifying antigens which are produced by infected cells, and the use of such antigens in immunogenic compositions or vaccines to treat or prevent infection.

2. Related Art

The immune system is the primary biological defense of the host (self) against potentially pernicious agents (non-self). These agents may be pathogens, such as bacteria or viruses, as well as modified self cells, including virus-infected cells, tumor cells or other abnormal cells of the host. Collectively, these targets of the immune system are referred to as antigens. The recognition of antigen by the immune system rapidly mobilizes immune mechanisms to destroy that antigen, thus preserving the sanctity of the host environment.

Antigens may provoke antibody-mediated responses and/or cell-mediated responses. Cells of the immune system termed B lymphocytes, or B cells, produce antibodies that specifically recognize and bind to the foreign substance. Other lymphocytes termed T lymphocytes, or T cells, both effect and regulate the cell-mediated response resulting eventually in the elimination of the antigen.

A variety of T cells are involved in the cell-mediated response. Some induce particular B cell clones to proliferate and to produce antibodies specific for the antigen. Others recognize and destroy cells that present foreign antigens on their surfaces. Certain T cells regulate the response by either stimulating or suppressing other cells.

Prospects for development of broadly effective tumor vaccines have been advanced by evidence that several self-proteins can be recognized as tumor antigens by immune T cells (Van den Eynde et al., *J. Exp. Med.* 173:1373 (1991); Bloom et al., *J. Exp. Med.* 185:453 (1997); Van Der Bruggen et al., *Science* 254:1643 (1991); Gaugler et al., *J. Exp. Med.* 179:921 (1994); Boel et al., *Immunity* 2:167 (1995); Van Den Eynde et al., *J. Exp. Med.* 182:689 (1995); Kawakami et al., *Proc. Natl. Acad. Sci. U.S.A.* 91:3515 (1994); Kawakami et al., *Proc. Natl. Acad. Sci. U.S.A.* 91:6458 (1994); Brichard et al., *J. Exp. Med.* 178:489 (1993)). Several genes and gene families that are expressed in melanoma and a fraction of tumors of other types but are silent in normal adult tissues except testis have been identified: MAGE-1 (van Der Bruggen, P., C. Traversari, P. Chomez, C. Lurguin, E. De Plaen, B. Van Den Eynde, A. Knuth, and T. Boon. 1991. Science 254: 1643–1647); MAGE-3 (Gaugler, B., B. Van den Eynde, P. van der Bruggen, P. Romero, J. J. Gaforio, E. De Plaen, B. Lethe, F. Brasseur, and T. Boon. 1994. J. Exp. Med. 179:921–930); BAGE (Boel, P., C. Wildman, M. L. Sensi, R. Brausseur, J. C. Renauld, P. Coulie, T. Boon and P. van der Bruggen. 1995. Immunity 2: 167–175); and GAGE (Van den Eynde, B., O. Peeters, O. De Backer, B. Gaugler, S. Lucas, and T. Boon. 1995. J. Exp. Med. 182: 689–698). In each case these gene products were identified by isolation of melanoma specific cytotoxic T cells from patients, and demonstration that the corresponding gene products are immunogenic.

Infected cells sometimes express self-proteins that are not expressed in uninfected cells. Geiss et al., *Virology* 266:8–16 (2000); Scheuring et al., *AIDS* 12:563–570 (1998).

SUMMARY OF THE INVENTION

The present invention provides a method of screening for therapeutics for infectious diseases, comprising identifying host cell gene products which are differentially expressed in infected cells, screening the differentially expressed gene products for immunogenicity, and determining which gene products are immunogenic.

The present invention also provides a method comprising identifying host cell gene products which are differentially expressed in infected cells, identifying which of the differentially expressed gene products are expressed embryonically, screening the differentially- and embryonically-expressed gene products for immunogenicity, and determining which gene products are immunogenic.

The differentially expressed gene products may be identified using subtractive hybridization, representational difference analysis, differential display, or ordered microarrays of nucleic acids.

Immunogenicity includes cytotoxic T lymphocyte responses, T helper responses, and B cell responses, such as antibody production.

BRIEF DESCRIPTION OF THE FIGURES

FIG. 1 shows the results of hybridization to an array of 24 cDNA clones selected following subtractive hybridization of cDNA from HIV-infected THP-1 monocytic cell line minus uninfected THP-1 cDNA + HIV DNA.

FIG. 2 shows hybridization to Northern blots of poly-A RNA from uninfected and HIV-infected cells.

DETAILED DESCRIPTION OF THE PREFERRED EMBODIMENTS

Altered features of an infected cell which are recognized by the immune system as non-self may be the basis for development of treatments or vaccines against infectious diseases. Since many pathogens elude immune surveillance by frequent reproduction and mutation, it is of considerable value to develop a vaccine that targets host gene products that are not likely to be subject to mutation. Thus, the present invention relates to a method of identifying potential therapeutics useful for the treatment or prevention of infectious diseases. By "treatment" is meant reduction in symptoms, reduction in pathogen load, reduction in the rate of pathogen replication, and/or no worsening of symptoms, pathogen load, or pathogen replication over a specified period of time.

Host gene products that are overexpressed in infected cells are identified. Those that are shown to be overexpressed by a factor of 9 or greater in infected cells as compared to uninfected cells are the most likely to be immunogenics. Optionally, relative gene expression is then determined in a broad panel of normal tissues. It is expected that immune tolerance will be induced to gene products expressed at relatively high levels in any normal tissue. Such gene products are excluded from further analysis. Immunogenicity is then directly assayed.

Thus, in one embodiment, a method is provided comprising identifying host cell genes which are differentially expressed in infected cells, screening the gene products of the differentially expressed host cell genes for immunogenicity, and determining which differentially expressed host cell gene products are immunogenic.

In another embodiment, a method is provided comprising identifying host cell genes which are differentially expressed in infected cells, identifying which of the differentially expressed genes are expressed in embryonic tissue, screening the gene products of said differentially- and embryonically-expressed genes for immunogenicity, and determining which differentially expressed host cell gene products are immunogenic. Developmentally regulated gene products are a very important pool of potential neoantigens since, once gene expression is turned off, it is no longer part of the definition of immunological "self" and tolerance is not maintained.

In another embodiment, a method is provided comprising identifying host cell genes which are differentially expressed in infected cells, identifying which of the differentially expressed genes are expressed in embryonic tissue, identifying which of the differentially and embryonically-expressed genes are not expressed in other adult tissues, screening the gene products of said differentially- and embryonically-expressed genes which are not expressed in adult tissue for immunogenicity, and determining which differentially expressed host cell gene products are immunogenic.

In another embodiment, a method is provided comprising identifying host cell genes which are differentially expressed in infected cells, identifying which which of the differentially-expressed genes are not expressed in other adult tissues, screening the gene products of said differentially-expressed genes which are not expressed in adult tissue for immunogenicity, and determining which differentially expressed host cell gene products are immunogenic.

Any cell type that is capable of being infected can be used in the method of the invention. Suitable cells include, but are not limited to, mammalian cells, including animal (rodents, including mice, rats, hamsters and gerbils), primates, and human cells, including cells of all types, including breast, skin, lung, cervix, colorectal, leukemia, brain, etc.

Cells include dividing cells, non dividing cells, terminally differentiated cells, pluripotent stem cells, committed progenitor cells and uncommitted stem cells.

Cells and cell types also include muscle cells such as cardiac muscle cells, skeletal muscle cells and smooth muscle cells, myofibrils, intrafusal fibers and extrafusal fibers; skeletal system cells such as osteoblasts, osteocytes, osteoclasts and their progenitor cells.; and epithelial cells such as squamous epithelial cells, including endothelial cells, cuboid epithelial cells and columnar epithelial cells.

Cells that can be used in the method of the present invention also include nervous system cells such as neurons, including cortical neurons, inter neurons, central effector neurons, peripheral effector neurons and bipolar neurons; and neuroglia, including Schwann cells, oligodendrocytes, astrocytes, microglia and ependyma.

Additionally, endocrine and endocrine-associated cells may also be used such cells as pituitary gland cells including epithelial cells, pituicytes, neuroglia, agranular chromophobes, granular chromophils (acidophils and basophils); adrenal gland cells including epinephrine-secreting cells, non-epinephrine-secreting cells, medullary cells, cortical cells (cells of the glomerulosa, fasciculata and reticularis); thyroid gland cells including epithelial cells (principal and parafollicular); parathyroid gland cells including epithelial cells (chief cells and oxyphils); pancreas cells including cells of the islets of Langerhans (alpha, beta and delta cells); pineal gland cells including parenchymal cells and neuroglial cells; thymus cells including parafollulicular cells; cells of the testes including seminiferous tubule cells, interstitial cells ("Leydig cells"), spermatogonia, spermatocytes (primary and secondary), spermatids, spermatozoa, Sertoli cells and myoid cells; cells of the ovary including ova, oogonia, oocytes, granulosa cells, theca cells (internal and external), germinal epithelial cells and follicle cells (primordial, vesicular, mature and atretic).

Circulatory system cells are also included such cells as heart cells (myocardial cells); cells of the blood and lymph including erythropoietin-sensitive stem cells, erythrocytes, leukocytes (such as eosinophils, basophils and neutrophils (granular cells) and lymphocytes and monocytes (agranular cells)), thrombocytes, tissue macrophages (histiocytes), organ-specific phagocytes (such as Kupffer cells, alveolar macrophages and microglia), B-lymphocytes, T-lymphocytes (such as cytotoxic T cells, helper T cells and suppressor T cells), megaloblasts, monoblasts, myeloblasts, lymphoblasts, proerythroblasts, megakaryoblasts, promonocytes, promyelocytes, prolymphocytes, early normoblasts, megakaryocytes, intermediate normoblasts, metamyelocytes (such as juvenile metamyelocytes, segmented metamyelocytes and polymorphonuclear granulocytes), late normoblasts, reticulocytes and bone marrow cells.

Respiratory system cells are also included such as capillary endothelial cells and alveolar cells; as are urinary system cells such as nephrons, capillary endothelial cells, granular cells, tubule endothelial cells and podocytes; digestive system such as simple columnar epithelial cells, mucosal cells, acinar cells, parietal cells, chief cells, zymogen cells, peptic cells, enterochromaffin cells, goblet cells, Argentaffen cells and G cells; and sensory cells such as auditory system cells (hair cells); olfactory system cells such as olfactory receptor cells and columnar epithelial cells; equilibrium/vestibular apparatus cells including hair cells and supporting cells; visual system cells including pigment cells, epithelial cells, photoreceptor neurons (rods and cones), ganglion cells, amacrine cells, bipolar cells and horizontal cells are also included.

Additionally, mesenchymal cells, stromal cells, hair cells/follicles, adipose (fat) cells, cells of simple epithelial tissues (squamous epithelium, cuboidal epithelium, columnar epithelium, ciliated columnar epithelium and pseudostratified ciliated columnar epithelium), cells of stratified epithelial tissues (stratified squamous epithelium (keratinized and non-keratinized), stratified cuboidal epithelium and transitional epithelium), goblet cells, endothelial cells of the mesentery, endothelial cells of the small intestine, endothelial cells of the large intestine, endothelial cells of the vasculature capillaries, endothelial cells of the microvasculature, endothelial cells of the arteries, endothelial cells of the arterioles, endothelial cells of the veins, endothelial cells of the venules, etc.; cells of the connective tissue include chondrocytes, adipose cells, periosteal cells, endosteal cells, odontoblasts, osteoblasts, osteoclasts and osteocytes; endothelial cells, hepatocytes, keratinocytes and basal keratinocytes, muscle cells, cells of the central and peripheral nervous systems, prostate cells, and lung cells, cells in the lung, breast, pancreas, stomach, small intestine, and large intestine; epithelial cells such as sebocytes, hair follicles, hepatocytes, type II pneumocytes, mucin-producing goblet cells, and other epithelial cells and their progenitors of the skin, lung, liver, and gastrointestinal tract may be used in the methods of the present invention, preferably the selection and screening methods.

The method of the present invention can be used to screen for antigens which are differentially expressed in cells infected with any infectious agent, including viruses, fungal agents, mycobacteria, bacteria or parasitic agents.

In one embodiment, the cells are infected with human immunodeficiency virus (HIV). This method of vaccine development is broadly applicable to any infectious agent but especially to infectious agents that, like HIV, replicate or mutate rapidly, for example, hepatitis C virus and many RNA viruses (because they depend on RNA polymerases which are more error prone since they do not have a "proof-reading" function).

In other embodiments, the cells are infected with infectious agents causing chickenpox, shingles, rubella, influenza, rubeola, mumps, yellow fever, mononucleosis, rabies, acute viral gastroenteritis, poliomyelitis, subacute sclerosing panencephalitis, encephalitis, Colorado tick fever, pharyngitis, croup, bronchiolitis, viral pneumonia, pleurodynia, aseptic meningitis, keratitis, conjunctivitis, viral leukemias, rabies, polio, myocarditis, hepatitis A, hepatitis B, hepatitis C, hepatitis D, hepatitis E; and any infections caused by adenoviruses, coxsackieviruses, parainfluenza viruses, respiratory syncytial virus, reovirus, cytomegalovirus, Epstein-Barr virus, herpes simplex viruses, herpes-zoster-varicella virus, rhinoviruses, rotaviruses, papolomaviruses, enteroviruses, paramyxoviruses, parvoviruses, apthoviruses, Ebola virus, Marburg virus, vesicular stomatitis virus, coronaviruses, Lassa virus, lymphocytic choriomeningitis virus, Machupo virus, Junin virus, human papillomavirus, or poxviruses.

Further examples of viruses, include, but are not limited to the following DNA and RNA viral families: Arbovirus, Adenoviridae, Arenaviridae, Arterivirus, Birnaviridae, Bunyaviridae, Caliciviridae, Circoviridae, Coronaviridae, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza), Papovaviridae, Parvoviridae, Picornaviridae, Poxyiridae (such as Smallpox or Vaccinia), Reoviridae (e.g., Rotavirus), Retroviridae (HTLV-I, HTLV-II, lentivirus), and Togaviridae (e.g., Rubivirus). Viruses falling within these families can cause a variety of diseases or symptoms, including, but not limited to: arthritis, bronchiollitis, encephalitis, eye infections (e.g., conjunctivitis, keratitis), chronic fatigue syndrome, hepatitis (A, B, C, E, Chronic Active, Delta), meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia.

Moreover, parasitic agents include, but not limited to, the following families: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and *Trichomonas*. These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), Malaria, pregnancy complications, and toxoplasmosis.

Fungal pathogens include, but are not limited to *Candida albicans* and *pneumocystis carnii*. Mycobacterial pathogens include, but are not limited to, *M. tuberculosis, M. avium*.

Differential Expression

Host cell gene products which are "differentially expressed" in infected cells include gene products which are upregulated during infection, i.e., expressed in a cell during both infection and non-infection but at higher levels during infection; and those which are expressed in a cell only during infection.

In one embodiment, differential expression is determined by subtractive hybridization. Methods of subtractive hybridization are known in the art. See, for example, U.S. Pat. Nos. 5,827,658; 5,700,644; and 5,525,471.

In another embodiment, differential expression is determined by representational difference analysis (RDA). RDA is a subtractive hybridization based method applied to "representations" of total cellular DNA (Lisitsyn, N. and N., M. Wigler. 1993. Science 259: 946–951). The differential display methods of Liang and Pardee (1992, Science 257: 967–971) employ an arbitrary 10 nucleotide primer and anchored oligo-dT to PCR amplify an arbitrary subset of fragments from a more complex set of DNA molecules.

In another embodiment, differential expression is determined by the modified differential display described below.

In another embodiment, differential expression is determined using microarrays. Preferably, differential expression is determined using ordered microarrays of nucleic acids. Two color differential hybridization may be used. Methods of making and using microarrays are known in the art. See, e.g., Eisen and Brown, *methods in Enzymol.* 303:179–205 (1999); Bowtell, *Nature Genet. Suppl.* 21:25–32 (1999); Cheung et al., *Nature Genet. Suppl.* 21:15–19 (1999); Duggan et al., *Nature Genet. Suppl.* 21: 10–14 (1999); Lipshutz et al., *Nature Genet. Suppl.* 21:20–24 (1999); and U.S. Pat. Nos. 6,060,288; 6,060,240; 6,045,996; 6,033,860 and 6,004,755.

Gene expression in embryonic tissues is known to be more complex than in adult tissues. Many of these genes are downregulated in the adult and would, therefore, not be expected to induce tolerance in newly arising lymphocytes of the adult. If expression of any of these gene products is again upregulated in infected cells, as is known to happen for some such genes in cells that undergo tumor transformation, then these would encode antigens that could be targeted for immunotherapy. An ordered library of cDNA clones expressed during early embryonic development can be made. See, e.g., Tanaka et al., *PNAS* 97:9127–9132 (2000). Microarrays representing the ordered library can be produced and be employed to efficiently identify developmentally regulated genes that are overexpressed in infected cells. This is a powerful tool that greatly accelerates the process of identifying specific host genes that encode novel antigens in infected cells infected.

Identification of genes which are expressed in embryonic tissue and/or are not expressed in adult tissue can be done by any method known in the art. In one embodiment, Discovery Line™ RNA and Gene Pool™ cDNA (Invitrogen), which is either total RNA or first strand cDNA prepared from over 30 different human normal adult or fetal tissues, is screened for expression of the differentially expressed gene. Those sequences that are consistently expressed in infected cells but which have low or undetectable expression in diverse normal tissues especially thymus are more likely to be immunogenic.

Immunogenicity

"Immune response" encompasses humoral and cell-mediated immune responses, including, but not limited to, antibody response, cytotoxic T lymphocyte response, T helper response, inflammation, cytokine production, and complement. A gene product is immunogenic if it induces one or more of these immune responses.

The ability of a differentially expressed gene product to modulate an immune response can be readily determined by an in vitro assay. T cells for use in the assays include transformed T cell lines, such as T cell hybridomas, or T cells which are isolated from a mammal, e.g., from a human or from a rodent such as a mouse. T cells can be isolated from a mammal by known methods. See, for example, Shimonkevitz et al., *J. Exp. Med.* 158:303 (1983).

One way to demonstrate immunogenicity in humans is by stimulation of a primary T cell response in vitro. A suitable assay to determine if a gene product is capable of modulating the activity of T cells is conducted by coculturing T cells and antigen presenting cells. The most effective antigen presenting cells for stimulation of a primary immune response are dendritic cells (DC). In order to efficiently introduce antigen into DC, recombinants of vaccinia, retroviral, or adenoviral vectors are generated for the same gene product and employed DC infected with these vectors to alternately stimulate autologous human T cells. Alternate cycles of stimulation with different vectors minimize selection of a vector specific response and focus immune reactivity on the recombinant gene. Alternatively, the differentially expresssed gene product may be added to the culture medium. Production of IL-2 is measured. An increase in IL-2 production over a standard indicates the compound can stimulate an immune response and is immunogenic.

Thus, in one embodiment, immunogenicity is determined by cultivating T cells with antigen-presenting cells, adding a differentially expressed gene product to the cell culture, and measuring IL-2 production. In another embociment, immunogenicity is determined by cultivating T cells with antigen-presenting cells, transfecting the antigen-presenting cells with a vector expressing the differentially expressed gene product, and measuring IL-2 production.

Other in vitro assays of T cell activation include secretion of other cytokines (IFN-γ, TNF-α, GM-CSF) measured by ELISA, ELISpot, or flow cytometric detection (Luminex bead system). Many of these methods are described in Current Protocols in Immunology (John Wiley & Sons, New York).

Alternatively, rather than measurement of an expressed protein such as IL-2, modulation of T cell activation can be suitably determined by changes in antigen-dependent T cell proliferation as measured by radiolabelling techniques or calorimetric MTT assay as are recognized in the art. For example, a labeled (e.g., tritiated) nucleotide may be introduced to an assay culture medium. Incorporation of such a tagged nucleotide into DNA serves as a measure of T cell proliferation. This assay is not suitable for T cells that do not require antigen presentation for growth, e.g., T cell hybridomas. A difference in the level of T cell proliferation following contact with the compound of the invention indicates the complex modulates activity of the T cells. An increase in T cell proliferation indicates the compound can stimulate an immune response.

Additionally, cytotoxic T lymphocyte (CTL) activity can be detected using a standard 4 hour $^{51}$Cr release assay, as well known in the art.

In vivo assays also may be suitably employed to determine the ability of a compound of interest to activate T cells. For example, a compound of interest can be assayed for its ability to inhibit immunoglobulin class switching (i.e. IgM to IgG). See, e.g., Linsley et al., *Science* 257:792–795 (1992)).

In vivo assays may also be suitably employed to determine the ability of a compound to induce antibody production. A compound of interest can be administered to a mammal such as a mouse, blood samples obtained from the mammal at the time of initial administration and several times periodically thereafter (e.g. at 2, 5 and 8 weeks after administration). Serum is collected from the blood samples and assayed for the presence of antibodies raised by the immunization. Antibody concentrations may be determined.

Alternatively, the differentially expressed genes may be screened for complement-dependent cytotoxicity (CDC) or antibody-dependent cellular cytotoxicity (ADCC). See U.S. Pat. No. 5,500,362 for ADCC and CDC assays.

In any complex mixture of potential immunogens, as would be present in an infected cell, some antigens will induce a strong response and others a weak response. This has important practical implications. A defect in antigen processing is not readily corrected with present methods, but a deficiency in T cell clonal expansion can be overcome by the most fundamental of all immunological manipulations—vaccination. Rather than examine what is immunogenic in an infected cell, it may be more profitable to evaluate what can become immunogenic if the representation of specific T cells is first augmented by vaccination. The most promising candidates for this purpose are the products of genes which are differentially expressed during infection.

Thus, in one embodiment, a method is provided comprising identifying genes which are differentially expressed in infected cells, followed by immunization with a the differentially expressed gene product or a recombinant expression vector comprising the differentially expressed gene, and isolation of CTL specific for one or more of these gene products. The immunogenicity of these peptide targets in man can be established by highly efficient in vitro stimulation of human T cells with autologous peptide-pulsed dendritic cells.

Cellular peptides derived by degradation of endogenously synthesized proteins are translocated into a pre-Golgi compartment where they bind to class I MHC molecules for transport to the cell surface. These class I MHC:peptide complexes are the target antigens for specific CD8+ cytotoxic T cells. Since all endogenous proteins turn over, peptides derived from any cytoplasmic or nuclear protein may bind to an MHC molecule and be transported for presentation at the cell surface. This allows T cells to survey a much larger representation of cellular proteins than antibodies which are restricted to recognize conformational determinants of only those proteins that are either secreted or integrated at the cell membrane. Class I-bound peptides are generally 8–10 residues in length and accommodate amino acids side chains of restricted diversity at certain key positions that match pockets in the MHC peptide binding site. These key features of peptides that bind to a particular MHC molecule constitute a peptide binding motif.

A major concern for the development of broadly effective human vaccines is the extreme polymorphism of HLA class I molecules. Extensive characterization of peptide binding motifs of different human class I MHC molecules has suggested that there are four major subtypes of HLA-A and HLA-B alleles such that many peptides will bind to multiple members of a single subtype. One attractive strategy, therefore, is to target representative members of these four subtypes: HLA-A2, HLA-A3, HLA-B7 and HLA-B44. Each subtype has an average representation across ethnic populations of between 40% and 50%. It is estimated that the combination of all four subtypes would cover 95% of the population.

Mice which are transgenic for human CD8 and a human HLA antigen can be used to determine whether a particular differentially expressed gene product is immunogenic in humans.

The invention will be better understood by reference to the specific embodiments detailed in the examples which follow.

EXAMPLES

Example 1

Representational Difference Analysis (RDA)

The PCR SELECT™ variation of RDA is marketed by Clontech (Palo Alto, Calif.). The following general protocol is a summary of the manufacturer's recommendations. cDNA is synthesized from both a tracer (represented by infected cell mRNA) and a driver (represented by parental, non-infected cell mRNA). "Representations" of both tracer and driver cDNA are created by digestion with RsaI which cuts the four-base recognition sequence GTAC to yield blunt end fragments. Adaptors, which eventually serve as primer sites for PCR, are ligated to the 5' ends of only the tracer cDNA fragments. Two aliquots of tracer representation are separately ligated with two different adapters. A series of two hybridizations are carried out. In the first set of hybridizations, each adapter ligated tracer sample is denatured and hybridized with a ten fold excess of the denatured representation of driver cDNA for 8 hours. Under these conditions re-annealing of all molecules is incomplete and some of both the high and low copy molecules remain single stranded. Since re-annealing rates are faster for more abundant species, this leads to normalization of the distribution through relative enrichment of low copy number single stranded molecules. The two hybridization reactions with each of the different adapter ligated tracer cDNA representations are then combined without fractionation or further denaturation but with addition of more freshly denatured driver in a second hybridization reaction that is allowed to proceed further to completion, approximately 20 hours.

An aliquot of the products from the second hybridization is used as a template for a high stringency PCR reaction, using the known sequences at the 5' ends of the ligated adapters as primers. The key here is that only tracer sequences that 1) remain single stranded through the first hybridization and 2) hybridize to a complementary tracer sequence ligated to the alternate adapter in the second hybridization can be exponentially amplified during PCR. This excludes both tracer and driver species that either remain single stranded or that have hybridized to excess driver (since they have a complementary primer at only one or neither end of the molecule), as well as tracer sequences that hybridize to a molecule with the same adapter (because the adapters are longer than the primers and hybridize to their own complement with higher affinity when it is present on the opposite end of a denatured single stranded molecule—a reaction termed "SuppressionPCR" by Clontech). Finally, a second high stringency PCR is performed using nested primers built into the adapters so as to further reduce background and enrich for differentially expressed sequences. The products of the second PCR are electrophoresed and visualized on an agarose gel. Individual bands are excised and subcloned for further analysis.

Example 2

Modified Differential Display of Genes Encoding Potential Immunogens

In the following example, the differential display methods of Liang and Pardee (1992, Science 257:967–971) were modified to improve resolution of DNA fragments and reduce the frequency of false positives.

The differential display method as originally described by Liang and Pardee (1992, Science 257:967–971) employs an arbitrary 10 nucleotide primer and anchored oligo-dT to PCR amplify an arbitrary subset of fragments from a more complex set of DNA molecules. In principle, differences among the fragments generated from normal and infected cells should reflect differences in gene expression in the two cell types. In practice, this method sometimes works well but often gives rise to numerous false positives. That is, bands which appear to be differentially displayed are, upon further characterization, found not to be differentially expressed. This is presumably due to variable PCR amplification of individual species in complex populations and a relatively high background that can obscure less prominent bands. Since considerable effort is required to establish differential expression, these endemic false positives are costly in terms of efficiency and productivity.

A single arbitrary primer may also be used for differential display, as described by Welch et al. Use of single primers does, however, require synthesis of a much larger set of independent primers to achieve the same coverage of a complex cDNA population.

In order to improve the resolution of fragments and reduce the frequency of false positives, a second arbitrary primer is substituted for the anchored oligo-dT employed in PCR amplification. This results in fewer DNA products in each PCR reaction so that individual DNA fragments can be more reliably resolved on sequencing gels.

Because each subset of fragments generated in this modified differential display protocol is a smaller representation of total cDNA, more primer pairs are required for adequate sampling. Employing the negative binomial distribution, it can be predicted that if 12 independent primers are utilized in all 66 possible primer pair combinations there is a greater than 85% probability that for an average size eukaryotic cDNA at least one primer pair will amplify a representative PCR fragment of size $\geq$ 70 bp.

Following is a lists of sequences of 12 arbitrary decamers from which primer pairs are selected for modified differential display. The specific primers were chosen on the basis of their sequence diversity, 3' hybridization affinity, and minimal pair-wise hybridization.

| TAC AAC GAG G | MR_1 | (SEQ ID NO:1) |
| GTC AGA GCA T | MR_2 | (SEQ ID NO:2) |
| GGA CCA AGT C | MR_5 | (SEQ ID NO:3) |
| TCA GAC TTC A | MR_7 | (SEQ ID NO:4) |
| TAC CTA TGG C | MR_8 | (SEQ ID NO:5) |
| TCG GTC ACA G | MR_9 | (SEQ ID NO:6) |

| | | -continued | |
|---|---|---|---|
| ATC TGG TAG A | | MR_10 | (SEQ ID NO:7) |
| CTT ATC CAC G | | MR_11 | (SEQ ID NO:8) |
| CAT GTC TCA A | | MR_12 | (SEQ ID NO:9) |
| GAT CAA GTC T | | MR_14 | (SEQ ID NO:10) |
| TGT CAC ATA C | | MR_15 | (SEQ ID NO:11) |
| CTG ATC CAT G | | Ldd1 | (SEQ ID NO:12) |

A separate cDNA synthesis reaction with 0.1 μg polyA-RNA and Superscript II Reverse Transcriptase (Gibco/BRL) is carried out with each primer. Five percent of the cDNA product made with each member of a primer pair is mixed together with that primer pair for amplification in 30 PCR cycles using Klen Taq Polymerase Mix (Clontech). The PCR primers are used for cDNA synthesis to avoid the 3' bias imposed by oligo-dT primed cDNA synthesis. The relative orientation of the two primers in cDNA is randomized by carrying out a separate synthesis with each primer. These cDNA can be mixed in the same combinations as the primers chosen for PCR amplification. PCR amplified cDNA fragments are resolved on 6% acrylamide gels and dried for autoradiography. Those bands which are differentially displayed in at least 2 infected cells samples samples and not in the parental cells are cut out and rehydrated. An aliquot (⅕) of the DNA recovered is reamplified using the same primer set and the same PCR conditions but without addition of isotope. This second PCR product is resolved on 1% agarose and individual bands are recovered by incubation with β agarase I (Gibco/BRL). Each DNA fragment recovered is cloned by blunt end ligation into the pcDNA3.1/Zeo (+) phagemid vector (Invitrogen). Since it is possible that a single band may include more than one molecular species, at least 4 different transformants with an insert of appropriate size are picked for further characterization. Northern analysis, RNase protection assays and semi-quantitative PCR are employed to confirm differential expression.

Example 3

Selection of Full Length cDNA Encoding Potential Immunogens

This section presents methods for facilitating selection of corresponding full length cDNAs from fragments of differentially expressed genes identified by representational difference analysis or by modified differential display. A single stranded biotinylated probe is synthesized from isolated cDNA fragments and is used to select the longer cDNA that contain a complementary sequence by solution hybridization to single stranded circles rescued from a phagemid infected cell cDNA library. This method is especially well-suited to the use of DNA fragments isolated by the modified differential display method employing two arbitrary primers. The same arbitrary primers employed for PCR amplification of a given fragment in differential display can be modified to generate a single stranded hybridization probe from that fragment. This avoids the need to sequence, select and synthesize a new pair of fragment specific primers for each new fragment of interest.

i) The two oligonucleotides of a pair of PCR primers employed in differential display are modified: (biotin-dT)-dT-(biotin-dT) is incorporated at the 5' end of one primer and a phosphate is incorporated at the 5' end of the second primer. These modified primers are incorporated by PCR into the two strands of a differential display fragment that was selected following the original PCR amplification with the same unmodified arbitrary primers. From this double stranded PCR product, the strand labelled with a 5' phosphate is digested with λ exonuclease to generate a single stranded biotin-labeled probe.

ii) Single stranded (ss) DNA circles are rescued from a phagemid cDNA library using the M13K07 packaging defective phage as helper virus. This library is constructed in the pcDNA3.1/Zeo(+) phagemid (Invitrogen, Carlsbad, Calif.) with insertion of (ApaI)oligo-dT primed cDNA between the Apa I and Eco RV restriction sites. A key manipulation to achieve the efficient ligation necessary for construction of a high titer cDNA library is to insure that cDNA inserts are 5' phosphorylated by treating with T4 polynucleotide kinase prior to ligation. The biotin-labeled single stranded probe generated from the differential display fragment is hybridized in solution to the ssDNA circles of the phagemid library. The biotin-labeled hybridization complexes can then be separated from unrelated ssDNA on streptavidin magnetic beads and the ss circles eluted for further analysis.

Example 4

The Use of Ordered Microarrays to Identify Gene Expression

A powerful recent development for analysis of differential gene expression is the use of ordered microarrays of cDNA in two color differential hybridization. Schena et al., Science 270:467–470 (1995); Schena et al., PNAS 93:10614–10619 (1996); and DeRisi et al., Nature Genetics 14:457–460 (1996).

The microarrays maybe used to determine differential gene expression in infected and uninfected cells. The microarrays may also be used to determine expression patterns of genes in adult and embryonic tissue.

The probe for the microarrays is prepared as follows:

| | Amount | Company | Final Concentration |
|---|---|---|---|
| 5 X First strand buffer | 80 μl | Gibco | 1X |
| pd(T) 12–18, 1 mg/ml | 10 μl | Pharmacia | 25 μg/ml |
| 5 mM dA, T, GTP | 40 μl | Pharmacia | 0.5 mM |
| 0.1 M DTT | 40 μl | | 10 mM |
| Rnase Inhibitor, 40 units/ul | 20 μl | Boehringer | 2 units/μl |
| 250 uCi alpha-33P dCTP | 25 μl | Amersham | |
| 150 ug RNA | 150 μl | | |
| water | 15 μl | | |
| final volume | 380 μl | | |

One reaction is made for two sets of membranes (one set contains 7 blots, A–G) or two reactions for 3 sets of membranes.

190 μl is aliquoted per 0.5 ml tube. Tubes are put in thermocycler: 65° C. for 10 minutes; 1° C. for 75 seconds; repeat for 23 cycles; and cooled down to 42° C. 10 μl Superscipt II Reverse transcriptase/tube (Gibco) is added. The tubes are incubated at 42° C. for 45 minutes. Another 10 μl Superscipt II Reverse transcriptase/tube (Gibco) is added. The tubes are incubated another 45 minutes at 42° C. Added to each tube are: 25 μl Superscript II Reverse transcriptase;

25 µl 0.5 M EDTA; and 50 µl 1 M NaOH; the tubes are incubated at 65° C. for 20 minutes. 12.5 µl 1 M Tris-HCl, pH 7.5 is added. 1 µl is removed for "Total cpm", and added to 3 mL ECO-scinct (Bio-Rad).

The remaining probe is purified on Bio-spin 6 columns, using 8 columns per probe. The caps are snapped from bottom, then the top of column is removed. The column is drained by gravity, and the flowthrough is discarded. The column is spun at 1000×g, for 2 min. The column is transferred to a fresh collection tube, add 70 µl/column and spun 1000×g, 2 minutes. The flow through is pooled from all columns, and 1 µl is counted in 3 ml ECO-scint.

Mycrohybe (Research Genetics) is warmed to hybridization temperature. For two sets: 43 ml Microhybe, 0.5 ml denatured salmon sperm DNA 5 mg/ml stock. Membranes are wet in 2×SSC for 5 minutes. Membranes are placed in 15 µl Falcon screw cap conical with 3 ml/tube and incubated 3–4 hours at 55–65° C. for prehybridization.

CoT DNA, yeast tRNA, and probe is denatured for 5 minutes at 99° C., then placed on ice. For two sets, 0.5 ml 50 mg/ml Poly A(Pharmacia) is mixed to a final concentration of 1 mg/ml; 0.5 ml 1 mg/ml human CoTl DNA (Gibco), to a final concentration of 17 µg/ml; 0.5 ml 50 mg/ml yeast tRNA (Sigma), to a final concentration of 1 mg/ml; 6 ml 50% dextran sulfate, to a final concentration of 10%; 22.5 ml Microhybe; and 0.6 ml probe. Pre-hybe is discarded, and 2 mL hybe solution/tube is added and incubated at 55–65° C. overnight.

The membranes are rinsed 1× at room temperature with 250 ml 2×SSC/0.5% SDS altogether in one container, followed by incubation 2× for 25 minutes at room temperature with 250 ml 2×SSC/0.5% SDS altogether in one container. The membranes are then incubated 2× for 30 minutes at 65° C. with 2×SSC/0.5% SDS, 3 ml/tube (one membrane/tube). The membranes are incubated 2× for 30 minutes at 65° C. in O. 1×SSC/0.5% SDS 3 ml/tube (one membrane/tube).

The membranes are wrapped in plastic wrap and exposed to phosphorimager for 10 days.

Example 5

In Vitro Assay for Determination of CTL Response to Differentially Expressed Gene Products To determine whether the products of differentially expressed genes are immunogenic, groups of three (HLA-A2.1×huCD8)$F_1$ transgenic mice are immunized intravenously with $5 \times 10^6$ pfu of each recombinant vaccinia virus which express the differentially expressed gene of interest (Bennink and Yewdell, 1990, Current Topics in Microbiol. and Immunol. 163: 153–178). After at least two weeks, mice are sacrificed and CD8+ splenic T cells are enriched on anti-CD8 coated magnetic beads. CD8+ cytolytic precursors are restimulated in vitro with parental SV-HUC cells that are transfected with the recombinant differentially expressed gene previously isolated in the pcDNA3.1/Zeo(+) plasmid expression vector. Substitution of the plasmid recombinant in place of the vaccinia vector for restimulation in vitro is necessary to avoid a large vaccinia vector specific response. After five days in vitro culture, cytolytic activity is determined by $^{51}$Cr release from SV-HUC target cells transfected with either the specific recombinant plasmid or a control ovalbumin gene recombinant.

Example 6

In Vitro Assay for the Immunogenicity of Differentially Expressed Gene Products Using Dendritic Cells Dendritic cells (DC) are the most potent stimulators of T cell responses identified to date. To test immunogenicity of differentially expressed gene products, DC are incubated with the relevant gene products and assayed for the ability to activate human autologous T lymphocytes.

Immature dendritic cells are prepared from healthy donors according to the method of Bhardwaj and colleagues (Reddy, A. et al.,. Blood 90:3640–3646 (1997)). Briefly, PBMC are incubated with neuramimidase-treated sheep erythrocytes and separated into rosetted T cell (ER+) and non-T cell (ER–) fractions. The ER+ fraction is cryopreserved for later use. The ER- fraction ($2 \times 10^6$ cells per well) is cultured in serum-free RPMI medium containing 1000U/ml rhGM-CSF, 1000 U/ml rhIL4 and 1% autologous plasma. This medium is replenished every other day. At day 7, the non-adherent immature DC are harvested from the culture and re-plated in maturation conditions (1000 U/ml GM-CSF, 1000 U/ml IL4, 1% autologous plasma and 12.5–50% monocyte-conditioned medium) for 2–4 days. Cells manipulated in this manner have morphological and surface characteristics (CD83+) of mature DC.

Mature (or immature) DC are pulsed with the gene products of the interest for a short period followed by cocultivation with autologous T cells in 24-well plates for a period of 7–14 days. In some experiments, these may be total T lymphocytes, but it may also be desirable to fractionate CD4 and CD8 cells using magnetic separation systems (Miltenyi Biotech). Total T lymphocytes are incubated with the appropriate antibody-magnetic bead conjugates to isolate total CD4, CD8, naïve CD4+CD45RA+, naïve CD8+CD45RA+, memory CD4+CD45RO+ or memory CD8+CD45RO+lymphocytes. For naive CD4 and CD8 lymphocytes, a cytokine cocktail consisting of IL-2 (20 U/ml), IL-12 (20 U/ml), IL-18 (10 ng/ml), IFN-gamma (1 ng/ml) and a monoclonal antibody specific for IL-4 (50 ug/ml) is especially potent in enhancing DC activation of cytotoxic T cells in vitro. At the end of the incubation period, the DC are washed and cultured in maturation conditions (1000 U/ml GM-CSF, 1000 U/ml IL-4, 1% autologous plasma and 12.5% monocyte-condition medium) for 2–4 days. Cells manipulated in this manner are viable and have morphological and surface characteristics (CD83+) of mature DC. Following the activation period, CTL activity is assessed in a 4 hour $^{51}$Cr release assay.

An efficient means to express a specific gene product for presentation by dendritic cells is through infection with a recombinant viral vector. Human DC infected with either retroviral, vaccinia, or adenoviral vectors recombinant for the same foreign gene are employed to alternately stimulate autologous human T cells. Cycling T cell stimulation with different vector recombinants significantly reduces the strong anti-vector response and promotes outgrowth of CTL specific for the recombinant gene product of interest (Chaux, P. et al.,. J. Immunol. 163:2928–2936 (1999)).

Dendritic cells from a normal donor can be transduced with a retroviral rector containing a gene differentially expressed in an infected cell. These infected DC are employed to stimulate autologous T cells in vitro. After 12 days, T cells are restimulated in the presence of IL-2 (20U/ml), IL-12(20 U/ml), and IL-18(10 ng/ml) with DC from the same donor infected with a vaccinia virus recombinant of the differentially expressed gene (MOI=1, 16 hours). A third cycle of stimulation is subsequently carried out with DC infected with an adenoviral recombinant of the differentially expressed gene. Specific lysis of infected target cells by the T cells stimulated in vitro with DC infected by recombinant vectors is measured.

Example 7

Differential Expression of Host Gene Products in HIV-1 Infected Monocytic Cells

In this example, deregulated gene expression in HIV-1 infected cells is identified that might give rise to novel antigens encoded by the host rather than the virus. In contrast to highly mutable viral antigens, host encoded antigens are expected to be a relatively stable target for protective immune responses and would not have any of the risks associated with immunization with attenuated virus.

Subtractive hybridization was employed to identify genes differentially expressed in IV-1 infected vs. uninfected cells. HIV-1 genes are naturally differentially expressed in HIV-1 infected cells. To eliminate HIV genes from consideration and control for subtraction efficiency, the subtraction driver was spiked with 1% HIV sequences.

FIG. 1 shows the results of hybridization to an array of 24 cDNA clones selected following subtractive hybridization of cDNA from infected THP-1 monocytic cell line minus uninfected THP-1 cDNA+HIV DNA. Three different probes were employed to test for differential gene expression: HIV genomic DNA from a plasmid vector, cDNA from the normal uninfected THP-1 monocytic cell line, and cDNA from HIV-1 infected THP-1. Only one clone in this set, B1, hybridized to the HIV probe (top panel). Seven clones gave detectable hybridization to the uninfected cDNA probe (middle panel). These included one, G3, which appeared to be downregulated in HIV-1 infected cells (compare bottom panel). As can be seen by comparing bottom and middle panels, a larger number of clones selected by subtractive hybridization demonstrate the expected preferential hybridization to a cDNA probe from infected cells.

Individual clones from this and other groups were tested by hybridization to Northern blots of poly-A RNA from uninfected and infected cells. The results for several representative clones are shown in FIG. 2 (these derive from a different set than those illustrated in FIG. 1, but illustrate the same patterns of expression). Clone 296 is, like clone B1 in FIG. 1, an unsubtracted HIV sequence. Clones 85a and 49 represent known genes, CTP synthetase (bands at approximately 7 kb and 4 kb) and tricarboxylate carrier (approximately 5 kb), that are significantly overexpressed in the infected cells. Clone 89 (2.5 kb) is a novel sequence of unknown function, but, by normalizing the RNA loaded in each lane to the relative expression of housekeeping genes (actin and G3PDH), clone 89 was found to be overexpressed in infected cells by only a factor of three relative to uninfected cells.

Example 8

Immunogenicity of Gene Products Differentially Expressed in HIV-infected Cells

There would be three major advantages to an AIDS vaccine based on alterations in host gene expression during HIV-1 infection rather than on gene products of the HIV virus itself. 1) Since the fidelity of host gene replication is far greater than that of HIV-1 and, especially, since host genes do not replicate with anything like the frequency of the HIV-1 genome, antigens encoded by host genes would represent a relatively stationary target much less prone to immune evasion through mutation. 2) Since key regulatory genes of HIV-1, rev, tat, and nef, are expressed early in the infectious cycle and may also be expressed in some persistently infected cells, host cell antigens induced through expression of these regulatory genes might enable the immune system to also target these reservoirs of latent infection. This has taken on increased importance since, as noted above, it is now known that important reservoirs of infection are resistant to triple drug therapy. 3) A vaccine that targets deregulated host gene products that are not expressed in normal uninfected cells would not have any of the risks associated with use of an attenuated viral vaccine (for example, that its activity might be reconstituted by recombination with another viral genome).

Evidence for transactivation of cellular genes by human retroviruses has been reported for both HIV-1 and HTLV-1. Rosenblatt, et al., 1995, Curr. Topics in Micro. Immunol. 193:25–49. Two early viral gene products, tat and rev, are central to transactivation. Tat stimulates HIV-1 gene expression during transcription initiation and elongation. Tat functions primarily through specific interactions with TAR, the transactivation response element downstream of the transcriptional start site, and several cellular cofactors to increase the processivity of RNA polymerase II complexes during HIV-1 transcription elongation. Suggestive evidence for potential regulatory interactions of tat with host genes include at least two human mRNA that have been reported to contain TAR-like sequences as well as the existence of a cellular protein, TRP-2, which has been shown to bind to the functional tat-binding trinucleotide bulge on TAR. A number of different cellular proteins, including transcription factors Sp-1 and TFIIF, have been found to bind directly to tat protein. Other cellular proteins have been shown to bind to either the Rev Response Element, RRE, or directly to the rev protein. Such interactions may lead directly or indirectly to deregulated expression of host genes and that some of these host gene products may give rise to immunogenic targets in HIV-1 infected cells that could be the basis for immunotherapeutic intervention.

For optimal sensitivity, it is necessary that a large fraction of the cell population be infected. Initial experiments focus on altered host gene expression following HIV-1 infection of GHOST clone 3 and U87MG derived cell lines that express high levels of both CD4 and CCR5 co-receptors. Observations of altered host gene expression can then be confirmed or extended in monocytic and T cell lines. In order to obtain the same high frequency of infection in these latter cell lines, the HIV-1 env(−) mutant is pseudotyped with the broad-host-range vesicular stomatitis virus envelope glycoprotein G (VSV-G). Host gene expression is be characterized following infection with both rev(+) and rev(−) virus. The rev(−) mutants express early regulatory genes of HIV-1 that have been shown to also be expressed in some latently infected cell lines. If immunogenic molecules can be identified among genes expressed early in infection, then this might make it possible to target the reservoir of latently infected cells that appears to escape other forms of therapy. The rev(+) virus expresses, in addition to rev, late HIV-1 accessory genes, vpu, vif, vpr and gag that may induce further quantitative or qualitative changes in host gene expression.

The most efficient and reliable way to determine immunogenicity; is to employ human dendritic cells pulsed with immunodominant peptides for stimulation of autologous human T cells in vitro. However, in order to identify immunodominant peptides, it is necessary to first induce specific T cells. It is first determined whether a gene product is potentially immunogenic by the ability to induce specific CTL in HLA-A2 and human CD8 double transgenic mice. The murine T cells selected are then be tested for crossreactivity on HIV-1 infected and uninfected targets. If differential reactivity is confirmed, then the same T cells can be employed to identify which of the peptide sequences that express an HLA binding motif in that gene product are immunodominant. It is then be possible to determine whether human T cells are capable of responding to these identified peptides presented by mature autologous dendritic cells or whether they may have been rendered tolerant perhaps due to expression of related gene products in other normal tissues.

Genes which are differentially expressed in HIV-infected cells are identified using microarrays, the PCR SELECT™ cDNA subtraction method (Clontech Laboratories), or the modified version of differential display method described above may be used to identify differentially expressed genes. Microarrays have been used to monitor host cell gene expressioin in HIV infected cells. Geiss et al., *Virol.* 266: 8–16 (2000).

In the present example, immunogenic peptides which bind HLA-A2.1 are identified. However, the experiments used in this example can also be used to identify immunogenic peptides which bind to the A3, B7 and B44 subtypes.

To facilitate identification of genetic interactions between virus and host, cells from which RNA is readily and reproducibly available for cDNA synthesis and Northern analysis are employed, such as the human THP-1 monocytic cell line (ATCC, TIB 202). This cell line shares more phenotypic and functional markers with normal mature monocytes than most other available monocytic cell lines. THP-1 is Fc receptor positive and phagocytic and provides costimulator activity for T cell responses to Con A. THP-1 expresses several other histologic and enzymatic markers of monocytes, most notably HLA-DR, and treatment with 160 nM phorbol diester (TPA) induces THP-1 to differentiate into cells with the functional characteristics of mature macrophage. IV-1 infection of THP-1 has been previously reported. Shattock, et al., *J. Virol.* 67:3569–3575 (1993). It is especially useful that THP-1 expresses HLA-A2 (haplotype: HLA-A2, A9, B5, DRW1, and DRW2).

Gene expression in HIV-1 infected and uninfected THP-1 that are untreated or TPA induced is compared. If specific gene deregulation associated with HIV-1 infection is identified in this monocytic cell line, it will be of great interest to determine whether similar alterations of gene expression are induced in HIV-1 infected T cell lines. Sup-T1 and CEM are suitable T cell lines in which to investigate these effects. Both lines are available from the AIDS Research Reagent Repository.

To enhance the efficiency of HIV-1 infection HIV-1 env(−) mutants that have been pseudotyped with the vesicular stomatitis virus envelope glycoprotein G (VSV-G) are employed. Use of the VSV pseudotype has the advantage that the interaction of viral and host genes can be studied independently of membrane CD4 and chemokine receptor expression in the target cell. There is, however, a concern that some effects on gene expression may be mediated by VSV envelope interactions. Two controls are incorporated to identify possible effects of the VSV envelope alone or in concert with the HIV genome.

TBP-1 cells are also infected with a VSV-G pseudotyped defective MuLV based vector that expresses Thy-1.2 under the Moloney murine sarcoma virus LTR. This VSV-G pseudotyped defective MuLV vector is packaged by triple co-transfection of COS cells with the defective MuLV based plasmid (pSRLthy), together with the packaging and env(−) deficient MuLV gag and pol expression construct pSV(−)env(−)MLV, and with the VSV-G expression construct pHCMV-G. An et al., *J. Virol.* 71:1397–1404 (1997). This control should identify changes in host cell gene expression that can be attributed to the VSV envelope alone.

A number of cell lines have been modified to express high levels of CD4 and CCR5 co-receptor so that a high frequency of HIV-1 infection is feasible. Changes in gene expression induced by infection of CCR5 transfected GHOST clone 3 cells are compared with the HIV-1 NL4-3 strain and with VSV-G pseudotyped NL4-3 genome. This control should identify changes in host cell gene expression that can be attributed to interaction between the VSV envelope and the HIV-1 genome.

The temporal pattern of HIV-1 RNA expression in the course of infection has been well characterized. The transition from multiply spliced to singly spliced and unspliced transcripts is a key event that has been shown to be blocked in some chronically infected cell lines. Butera et al., *J. Virol.* 68:2726–2730 (1994); Cannon et al., *J. Virol.* 68:1993–1997 (1994). This form of blocked early-stage latency can be overcome by cellular activation with phorbol ester or cytokines and appears to be a result of either limited transcription at the site of proviral integration or an inherent deficiency in cellular regulatory factors. It has been suggested that a similar state of blocked early-stage latency may occur in some cells during the course of natural infection in vivo. Since viral mutants in rev give rise to the same pattern of RNA transcription characteristic of chronically infected cell lines, it will be interesting to investigate patterns of differential gene expression in cells infected with rev(−) mutants. In comparison to the study of chronically infected cell lines (e.g. U1/HIV-1) this has the advantage that specific effects on gene expression can be compared in different target cell populations infected with the same mutant virus and, importantly, that the immediately relevant uninfected cell controls are directly available for comparison.

Viral Mutants:

HIV-1$_{NL4-3}$env(−): An envelope-defective molecular clone of HIV-1$_{NL4-3}$ was constructed by deletion of the envelope gene sequences between two bglII restriction endonuclease sites. Planelles et al., *J. Virol.* 69:5883–5889 (1995). A related clone, HIV-1$_{NL4-3}$ Thy-1.2env(−), has the murine thymocyte Thy-1.2 surface antigen introduced into the nef open reading frame by deletion of the nef gene sequences between XhoI and KpnI sites. This clone is especially useful to determine the frequency of infected cells in a population.

HIV-1$_{NL4-3}$env(−)rev(−): The Rev open reading frame (orf) was disrupted by introducing an oligonucleotide encoding double stop codons in all 3 reading frames into the Rev gene. The insertion of this oligonucleotide would be into a BamHI site present in approximately the middle of the Rev orf. The BamHI site is at nucleotide position 7886 in the HIV provirus clone (DHIV-3nef). Unfortunately, this HIV provirus clone contained an additional BamHI site in the vector (not in the HIV DNA), at position 9143 (the HIV sequence in this vector is from position 1 to 9129). This extra BamHI site was removed by digesting DHIV-3nef with XmaI (position 9149) and XbaI (position 9131), blunt ending with pfu polymerase, and religating the DNA. The ligated DNA was transformed into XL-10 Gold bacteria and clones were identified that contained a unique BamHI site in the Rev gene. This clone is designated DHIV-3nef-BamHI (−).

In order to disrupt the Rev orf two single stranded, complementary oligonucleotides were synthesized and annealed together. This double stranded oligonucleotide encoded 5' BamHI sticky end/double stop codons (TAA) in all 3 reading frames/Eco RI site/Bam HI sticky end. This oligo was ligated into the Bam HI site of DHIV-3nef-BamHI (−). Following transformation, clones that contained the oligonucleotide were identified by restriction digest analysis using EcoRI. Sequence analysis confirmed that these clones contained the Rev knockout oligonucleotide. These clones were designated DHIV3-nef-Rev(−).

VSV-G pseudotyped env-deficient HIV-1 are produced by electroporation of COS-7 cells with p HIV-1$_{NL4-3}$ env(−) (or p HIV-1$_{NL4-3}$ env(−)rev(−)) and pHCMV-G, which expresses the VSV-G gene under the control of the CMV promoter (39). In the case of the rev(−) plasmid, triple cotransfection with pcRev provides the necessary rev functions in trans. Viral supernatants are harvested at 48 and 72 hrs and are titred by activation of the b-Galactosidase gene in the MAGI cell assay (40). It is expected, on the basis of prior experience with HeLa cells, that THP-1 infection with VSV-G pseudotyped HIV-1$_{NL4-3}$env(−) at m.o.i.=3 will result in greater than 75% infected cells. Control experiments will be carried out by infection of untreated and TPA induced THP-1 monocytic cells with VSV-G pseudotyped HIV-1$_{NL4-3}$ Thy-1.2env(−) to allow simple scoring of the frequency of infected cells by FACS analysis of Thy-1.2 expression.

Fresh primary monocytes are resistant to HIV-1 infection in vitro. Susceptibility to infection, however, increases rapidly during the first 24 hrs of in vitro culture. This appears to be related to differentiation induced by adherence to plastic. Viral yield from monocytic cultures can be greatly enhanced by addition of GM-CSF and M-CSF to promote differentiation. In order to compare host gene deregulation in HIV-1 infected THP-1 and normal monocytes, Ficoll/Hypaque isolated PBMC are resuspended at 5×10$^6$ cells/ml in RPMI with 10 mM HEPES and no serum in plastic tissue culture dishes for 2 hrs incubation at 37° C. Monolayers are carefully washed to remove all non-adherent cells (recovery is 10 to 20%, with >90% CD 14+CD3− cells). Cells are maintained in complete medium for 7 days in vitro prior to infection with VSV-G pseudotyped HIV-1$_{NL4-3}$env(−) (or HIV-1$_{NL4-3}$ env(−)rev(−)) at m.o.i.=3. Expression of specific genes previously identified as differentially expressed in HIV-1 infected THP-1 cells are determined by Northern blot and RNAse protection assays with RNA extracted from infected and uninfected primary monocyte cultures. Since THP-1 cells can be induced by GM-CSF as well as by TPA, an interesting variation on this experiment is to compare HIV-1 infected, GM-CSF induced THP-1 and GM-CSF activated primary monocytes (monocyte derived macrophage).

To determine the expression pattern in other normal adult and fetal tissues of any gene which is differentially expressed in HIV-1 infected monocytic cells, Discovery Line™ RNA and Gene Pool™ cDNA (Invitrogen) is used. Those sequences that are consistently expressed in HIV-1 infected monocytic cells but which have low or undetectable expression in diverse normal tissues especially thymus are more likely to be immunogenic.

Construction of Vaccinia Virus Recombinants

The ease of cloning and propagation in a variety of host cells has led to the widespread use of poxvirus vectors for expression of foreign proteins and as delivery vehicles for vaccine antigens. Recently, two laboratories have reported on a direct ligation protocol obviating the need for homologous recombination to generate poxvirus chimeric genomes. Merchlinsky et al., Virology 190: 522–526 (1992); Scheiflingler et al., Proc. Natl. Acad. Sci. USA 89: 9977–9981 (1992). In order to make this method more generally useful, a new direct ligation vector was constructed, vEL/tk, that incorporates unique NotI and ApaI restriction sites downstream of the early/late 7.5 k vaccinia promoter. This vector gives higher levels of expression of the recombinant gene, permits directional cloning of DNA, and largely eliminates the background of non-recombinant virus following ligation. Merchlinsky et al., 1997. Virology, 238: 444–451(1997).

HLA-restricted Response of Murine T Cells in HLA-A2/K$^b$ and Human CD8 Transgenic Mice The avidity of interaction between the cytolytic T cell receptor and MHC:peptide complex on the target cell must, in general, be enhanced by a parallel interaction between the CD8 molecule on the T cell membrane and MHC class I of the target. Since murine CD8 does not interact efficiently with human HLA class I, induction of HLA-restricted T cell responses in HLA-transgenic mice requires that either a second transgene for human CD8 be introduced or that the HLA molecule be modified to permit interaction with murine CD8. For HLA-A2.1, the latter can be accomplished by construction of a chimeric HLA molecule, HLA-A2/K$^b$, with the a1 and a2 domains of HLA-A2.1 and the a3 domain of murine H-2K$^b$. Co-expression of human CD8 in the HLA transgenic is desirable because CTL induced in these mice for crossreactivity on human HLA-2+, HIV-1-infected cells is tested. If the T cells did not express human CD8, then it is necessary to transfect the chimeric HLA-A2/K$^b$ gene even into target populations that express native HLA-A2.1. Double transgenic (HLA-A2/K$^b$×huCD8) F$_1$ hybrid mice are therefore used for induction of HLA-A2.1 restricted murine T cell responses.

HLA transgenic mice have been previously employed to characterize peptide epitopes of HTLV-1 in association with HLA-B35 (Schonbach et al., Virology. 226: 102–12 (1996)), and epitopes of Hepatitis C Virus (Shirai et al., J. Immunol. 154: 2733–42 (1995)), Human Papilloma Virus type 16 (Ressing et al., J. Immunol. 154:5934–43 (1995)), and circumsporozoite protein of *Plasmodium falciparum* (Blum-Tirouvanziam et al., J. Immunol. 154:3922–31) in association with HLA-A2.1. In these experiments as well as in a broad survey of the immune response of HLA-A2.1 transgenic mice to HLA-A2.1 binding peptides (Wentworth et al., Eur. J. of Immunol. 26: 97–101 (1996)), it was concluded that there is an extensive overlap between the T cell repertoire of mouse and man.

Vaccination with Vaccinia Virus Recombinant of Differentially Expressed Genes

To determine whether the products of differentially expressed genes are immunogenic, groups of three (HLA-A2/K$^b$×huCD8)F$_1$ transgenic mice are immunized intravenously with 5×10$^6$ pfu of vaccinia virus recombinant for a differentially expressed gene. Bennink et al., Current Topics in Microbiol. and Immunol. 163: 153–178 (1990). After at least two weeks, mice are sacrificed and CD8+ splenic T cells are enriched on anti-CD8 coated magnetic beads. CD8+ cytolytic precursors are restimulated in vitro with THP-1 monocytic cells that are transfected with the recombinant differentially expressed gene previously isolated in the pcDNA3.1/Zeo(+) plasmid expression vector. Substitution of the plasmid recombinant in place of the vaccinia vector for restimulation in vitro is necessary to avoid a large vaccinia vector specific response. After five days in vitro culture, cytolytic activity is determined by $^{51}$Cr release from THP-1 target cells transfected with either the specific recombinant plasmid or a control ovalbumin gene recombinant.

This same cytolytic assay can be readily applied to determine whether CTL epitopes are also presented by other HLA compatible HIV-1 infected cells. For T cells induced in (HLA-A2/K$^b$xhuCD8)F$_1$ transgenic mice, HLA compatible targets include cells that either express native HLA-A2.1 or that have been transfected with HLA-A2.1 (or HLA-A2/K$^b$).

In order to demonstrate immunogenicity, human dendritic cells pulsed with immunodominant peptides for presentation to autologous T cells in vitro are used. However, in order to identify immunodominant peptides, it is necessary to first induce specific T cells. A two-phase strategy can be used in which it is first determined whether a gene product is immunogenic by the ability to induce specific CTL in HLA-A2 and human CD8 double transgenic mice. The T cells selected will then be tested for crossreactivity on HIV-1 infected, HLA compatible tumors that express the corresponding mRNA and, if tumor reactivity is confirmed, will be used to identify which of the peptide sequences that express an HLA binding motif in that gene product are immunodominant. It will then be possible to determine whether human T cells are capable of responding to these identified peptides or whether they may have been rendered tolerant.

There are publicly available programs for identification of peptides in a given sequence that express a human or murine MHC binding motif. Parker et al., Journal of Immunology 152:163 (1994). Specific T cells can then be used to identify the immunodominant peptides. In the absence of tolerance, presentation of these peptides by mature dendritic cells (DC) is a very efficient means of stimulating primary, peptide-specific T cell responses in vitro.

It will be clear that the invention may be practiced otherwise than as particularly described in the foregoing description and examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

---

What is claimed is:

1. A method of screening for potential vaccine targets for infectious diseases, comprising:
   (a) identifying human gene products selected from the group consisting of: human gene products which are upregulated by a factor of 9 or greater during viral or mycobacterial infection and human gene products which are expressed only during viral or mycobacterial infection;
   (b) screening said human gene products for an immune response in humans;
   wherein said immune response is selected from the group consisting of: antibody response, cytotoxic T lymphocyte (CTL) response, T helper response, inflammation, and cytokine production, and wherein said gene products which induce an immune response in humans are potential vaccine targets for infectious diseases during which such upregulation or expression occurs.

2. The method of claim 1, wherein said human gene products which are upregulated by a factor of 9 or greater are expressed at a lower level in uninfected cells than in infected cells of the same type.

3. The method of claim 1, wherein said human gene products which are upregulated are not expressed at all in uninfected cells of the same type.

4. The method of claim 1, wherein said infection is infection with human immunodeficiency virus (HIV).

5. The method of claim 1, wherein said human gene products of (a) are identified using ordered microarrays of nucleic acids.

6. The method of claim 1, wherein said human gene products of (a) are identified using subtractive hybridization.

7. The method of claim 1, wherein said human gene products result from a mycobacterial infection.

8. The method of claim 1, wherein said human gene products result from a viral infection.

9. The method of claim 1, wherein said immune response is an antibody response.

10. The method of claim 1, wherein said immune response is a CTL response.

11. The method of claim 1, wherein said immune response is a T helper response.

12. The method of claim 1, wherein said immune response is inflammation.

13. The method of claim 1, wherein said immune response is cytokine production.

* * * * *